United States Patent
Gualtieri et al.

(10) Patent No.: US 7,966,862 B2
(45) Date of Patent: Jun. 28, 2011

(54) ELECTRODE STRUCTURE FOR PARTICULATE MATTER SENSOR

(75) Inventors: Devlin M. Gualtieri, Ledgewood, NJ (US); James Piascik, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 92 days.

(21) Appl. No.: 12/020,950

(22) Filed: Jan. 28, 2008

(65) Prior Publication Data

US 2009/0188300 A1    Jul. 30, 2009

(51) Int. Cl.
    *G01N 7/00* (2006.01)
(52) U.S. Cl. ............................. 73/28.01; 73/28.05
(58) Field of Classification Search .............. 73/28.01, 73/866.5, 28.05
    See application file for complete search history.

(56) References Cited

U.S. PATENT DOCUMENTS

| | | | |
|---|---|---|---|
| 3,869,703 A * | 3/1975 | Rowe et al. ................. | 257/746 |
| 4,021,326 A | 5/1977 | Pollner et al. | |
| 4,152,234 A | 5/1979 | Pollner | |
| 4,300,990 A | 11/1981 | Maurer | |
| 4,307,061 A | 12/1981 | Sarholz | |
| 4,339,320 A | 7/1982 | Friese et al. | |
| 4,485,794 A | 12/1984 | Kimberley et al. | |
| 4,656,832 A | 4/1987 | Yukihisa et al. | |
| 5,071,532 A * | 12/1991 | Taillet et al. ................. | 204/660 |
| 5,076,237 A | 12/1991 | Hartman et al. | |
| 5,180,983 A | 1/1993 | Murata et al. | |
| 5,243,252 A * | 9/1993 | Kaneko et al. ............... | 313/309 |
| 5,271,821 A | 12/1993 | Ogasawara et al. | |
| 5,681,986 A | 10/1997 | Merk et al. | |
| 5,889,196 A | 3/1999 | Ueno et al. | |
| 5,898,257 A | 4/1999 | Sequerra et al. | |
| 6,067,843 A | 5/2000 | Hafele et al. | |
| 6,192,740 B1 | 2/2001 | Thomas et al. | |
| 6,341,501 B2 | 1/2002 | Sugimoto et al. | |
| 6,432,168 B2 | 8/2002 | Schonauer | |
| 6,466,022 B1 | 10/2002 | Koopmans | |
| 6,512,375 B1 | 1/2003 | Yamada et al. | |
| 6,583,539 B1 | 6/2003 | Zamora | |
| 6,601,464 B1 | 8/2003 | Downing | |
| 6,634,210 B1 | 10/2003 | Bosch et al. | |
| 6,639,671 B1 * | 10/2003 | Liu .............................. | 356/336 |
| 6,849,238 B2 | 2/2005 | Weyl et al. | |

(Continued)

OTHER PUBLICATIONS

Quinn, David, et al., "II.C Enabling Technologies", *FY 2005 Progress Report, Advanced Combustion Engine Technologies*, (2005), 1-16.

(Continued)

*Primary Examiner* — Hezron Williams
*Assistant Examiner* — Rodney T Frank
(74) *Attorney, Agent, or Firm* — Schwegman, Lundberg and Woessner, P.A.

(57) ABSTRACT

A particulate matter detector formed in an insulated device such as a spark plug. The insulated device has a center electrode having a first end and a second end. The first end of the center electrode passes through the insulated device and may be connected to a terminal. The second end of the electrode is formed to provide a greater surface area. The form may be a star, circle, series of S's or a helix to increase the surface area of the second end of the center electrode that may be exposed to the exhaust from an engine. The sensor may be used to measure particulate matter in the exhaust of an engine and permit a processor to regulate the operation of the engine.

11 Claims, 7 Drawing Sheets

U.S. PATENT DOCUMENTS

| | | | |
|---|---|---|---|
| 6,948,353 B2 | 9/2005 | Toguchi et al. | |
| 6,949,874 B2 | 9/2005 | Schumann | |
| 6,971,258 B2* | 12/2005 | Rhodes et al. | 73/28.01 |
| 7,010,356 B2* | 3/2006 | Jog et al. | 607/116 |
| 7,155,334 B1 | 12/2006 | Stewart et al. | |
| 7,275,415 B2* | 10/2007 | Rhodes et al. | 73/28.01 |
| 7,389,773 B2* | 6/2008 | Stewart et al. | 123/672 |
| 7,549,317 B2* | 6/2009 | Rhodes et al. | 73/23.31 |
| 7,564,043 B2* | 7/2009 | Hayashi et al. | 250/397 |
| 7,628,007 B2* | 12/2009 | Kittelson et al. | 60/277 |
| 7,765,792 B2* | 8/2010 | Rhodes et al. | 60/278 |
| 2001/0051108 A1 | 12/2001 | Schonauer | |
| 2006/0016246 A1 | 1/2006 | Rhodes et al. | |
| 2006/0095105 A1* | 5/2006 | Jog et al. | 607/116 |
| 2006/0137346 A1 | 6/2006 | Stewart et al. | |
| 2007/0039589 A1 | 2/2007 | Stewart et al. | |
| 2007/0089399 A1* | 4/2007 | Rhodes et al. | 60/278 |
| 2007/0137177 A1 | 6/2007 | Kittelson et al. | |
| 2007/0142999 A1 | 6/2007 | Baramov et al. | |
| 2008/0265870 A1 | 10/2008 | Nair et al. | |
| 2009/0035870 A1 | 2/2009 | Ruiz | |
| 2009/0056416 A1 | 3/2009 | Nair et al. | |
| 2009/0113983 A1 | 5/2009 | Krafthefer | |

OTHER PUBLICATIONS

"U.S. Appl. No. 12/133,072, Non-Final Office Action mailed Jun. 2, 2009", 4 pgs.

"U.S. Appl. No. 12/020,950 Response to Restrictions", 6, mailed Jul. 29, 2009.

"U.S. Appl. No. 12/133,072, Notice of Allowance mailed Sep. 9, 2009", 3 Pgs.

"U.S. Appl. No. 12/133,072, Response filed Aug. 10, 2009 to Non Final Office Action mailed Jun. 2, 2009", 10 pgs.

* cited by examiner

ELECTRODE STRUCTURE FOR PARTICULATE MATTER SENSOR

BACKGROUND

Many combustion devices produce particulate emissions. For example, diesel engines are increasing in popularity in many kinds of vehicles. In the meantime, environmental regulations relative to particulate emissions are becoming more stringent. Thus, there is need for minimizing emissions from diesel engines and other particulate emitting mechanisms.

PM emissions contribute to the fine particle burden in the atmosphere. and the EPA has established a light-duty vehicle PM emission standard of 0.08 g/mile and has promulgated a regulation to limit the amount of particular matter with a diameter of 2.5 microns or less (such as the newer 0.1 micron standard being considered). To meet these standards, engine manufacturers have developed low-emission engines. Technological improvements may have reduced mass emissions, but it has been said the newer engines meeting the 1991 emissions limit requirements had dramatically increased numbers and volumes of very small nuclei mode particles when compared to similar engines meeting 1988 emissions limit requirements. These observations suggest that not only accumulation mode size particles, but also nuclei size particles may pose future emission problems.

Particulate matter (PM) sensors are used in internal combustion engines to determine combustion characteristics, particularly with respect to soot that results from incomplete combustion.

DETAILED DESCRIPTION

Figure 1A:
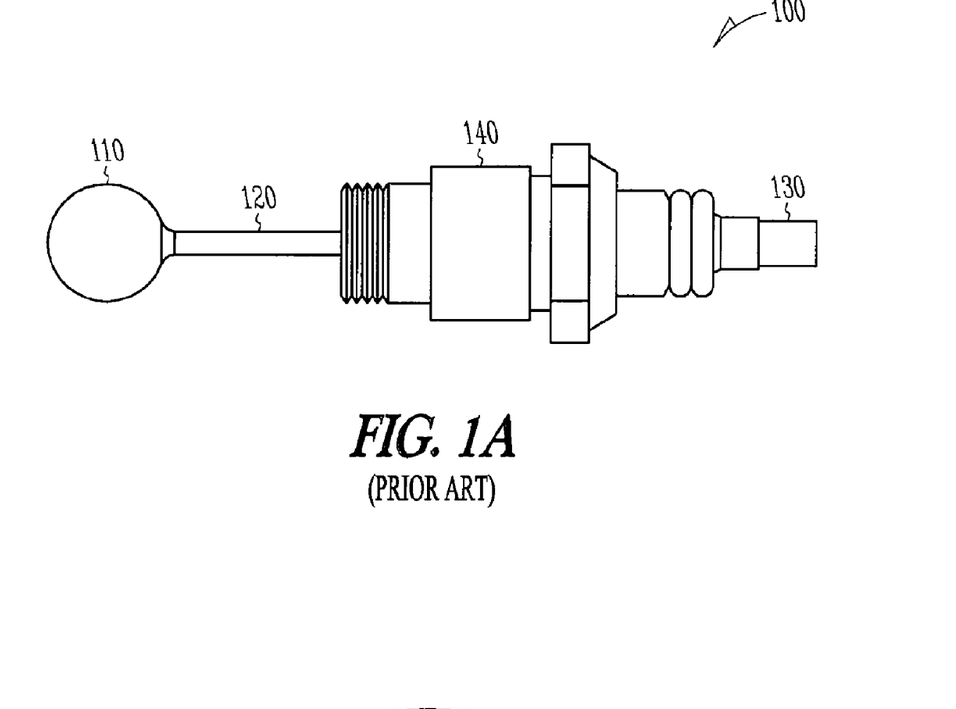
FIG. 1A is a prior art ball-on-stick particulate matter sensor.

FIG. 1A is a prior art ball on stick particulate matter sensor. The sensor 100 may be a spark-plug-like device having an extended center electrode 120 composed of a stainless steel or other material. The electrode 120 and ball 110 may have a thin passivating layer formed on it. The sensor 100 may detect charge transients indicative of particulate concentration in the exhaust stream. The sensor 100 may be built upon an automotive spark plug 140. Ball 110 of sensor 100 may be placed in the path of the exhaust of an engine. Ball 110 and electrode 120 may be passivated with a very thin nonconductive coating or layer. This coating or layer accounts for the lack of electrical shorting by the soot layer accumulated by ball 110 and electrode 120 during operation of the engine. The passivation material may be composed of silicon nitride ($Si_3N_4$), ceria and the like. The thickness of the passivation layer on ball 110 and electrode 120 may be between 0.001 and 0.100 inch. A nominal thickness may be about 0.01 inch. The passivation layer may be achieved with the exposure of the probe to high exhaust gas temperatures or may be coated with such layer via a material added to the engine fuel.

During the testing of a sensor of similar design as sensor 100 without ball 110 for vibration noise, a ball 110 was placed at the end of a sensor probe similar to electrode 120 to try and induce additional vibration to the sensor 100 and to see if any component of that vibration was due to pressure or velocity variances in the exhaust stream. No additional noise due to vibration was seen, but the signal amplitude increased by about 50% due to the increased surface area. It was determined that the ball-on-stick electrode 110 and 120 structure provides a large surface area at a favored point in the exhaust gas stream. The inventors however have determined that the ball on stick sensor 100 has added costs due to the expense and time of welding ball 110 onto sensor probe 120.

An embodiment of sensor 100 may be a standard spark plug 140 (such as a Champion™ RJ19LM, though the model is not important) that has the outside electrode removed and has a 4 to 6 inch stainless steel electrode 120 of about ⅛ inch diameter welded to the center electrode 130. A stainless steel ball 110 may then be welded to the other end of the electrode 120. The extended electrode 129 and ball 110 may be passivated as discussed above with a very thin non-conducting surface layer, so that the ball 110 and electrode 120 will develop an image charge from the exhaust particulates but will not be electrically shorted to the spark plug base 140 or the grounded exhaust pipe. The passivating layer may be deposited or grown on the electrode 120 and ball 110.

Figure 1B:
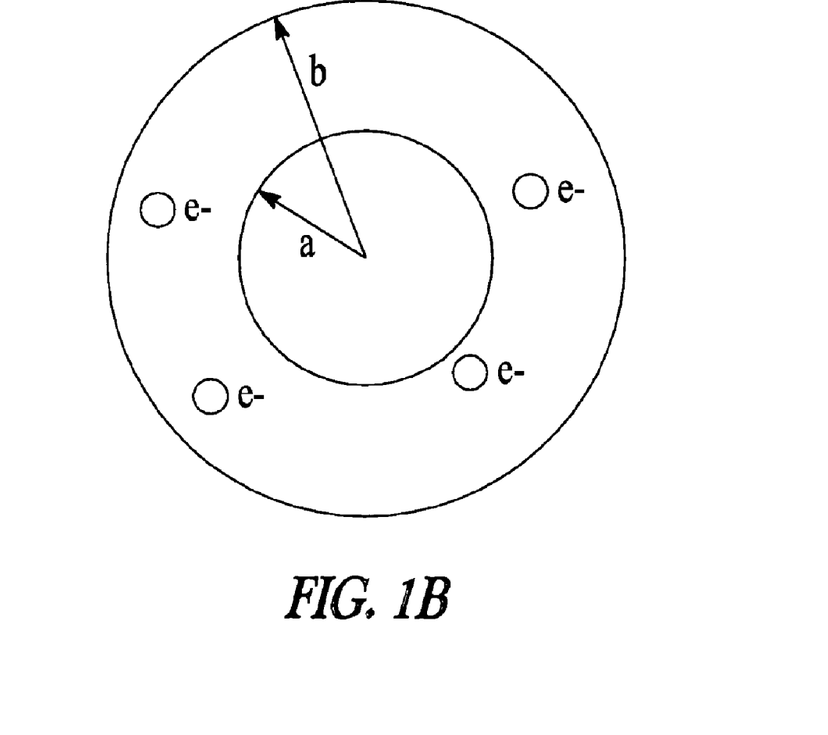
FIG. 1B shows a simplified model of the operation of the sensor.

FIG. 1B shows a simplified model of the operation of the sensor. The sensor operates as a capacitor formed by two concentric spheres. The inner sphere has radius a, and the outer sphere has radius b. The inner sphere corresponds to the sensor such as ball 110 of FIG. 1 and the outer sphere corresponds to the surrounding exhaust pipe. Charges present in the region between the spheres, shown here as individual electron charges, will produce a voltage between the spheres. The capacitance C of the concentric spheres is given as:

$$C=4\pi\epsilon_0(ab)/(b-a)$$

Where $\epsilon_0$ is the permittivity of free space, $8.854\times10^{-12}$ Farad/meter. For b>> a, we may simply the formula, as follows:

$$C=4\pi\epsilon_0 a$$

Since the area A of the inner sphere is:

$$A=4\pi(a^2)$$

Then:

$$a=(\tfrac{1}{2})A^{1/2}\pi^{-1/2}$$

This permits us to generalize the capacitance to the area of the inner sphere, and generalize further to the area of any probe geometry, such that:

$$C=2\pi^{1/2}\epsilon_0 A^{1/2}$$

A voltage "E" on a capacitor is given by the equation E=Q/C. Where Q is the capacitor charge. An electron change q is $-1.6\times10^{-19}$ Coulombs. This leads to the voltage produced by the presence of a single electron charge in the dielectric volume of the capacitor as given by the equation:

$$E = q/(2\pi^{1/2} \epsilon_0 A^{1/2})$$

Estimating for a probe area of about a square inch ($5 \times 10^{-4} m^2$), E equals $2.3 \times 10^{-7}$ volts.

The ball on stick particle sensor 100 of FIG. 1A utilizing the larger mass or ball 110 at the end of electrode 120 has been shown to provide very good results. However, the inventors have determine that the manufacture requirements of welding the ball 110 onto the rod portion of the electrode 120 assembly is complicated. The inventors propose, instead, to shape the end of the rod into a suitably large area before oxidation to obtain the dielectric layer. FIGS. 2-7 show some representative structures that can be used, although other, similar, structures may be apparent to those skilled in the art.

Figure 2:
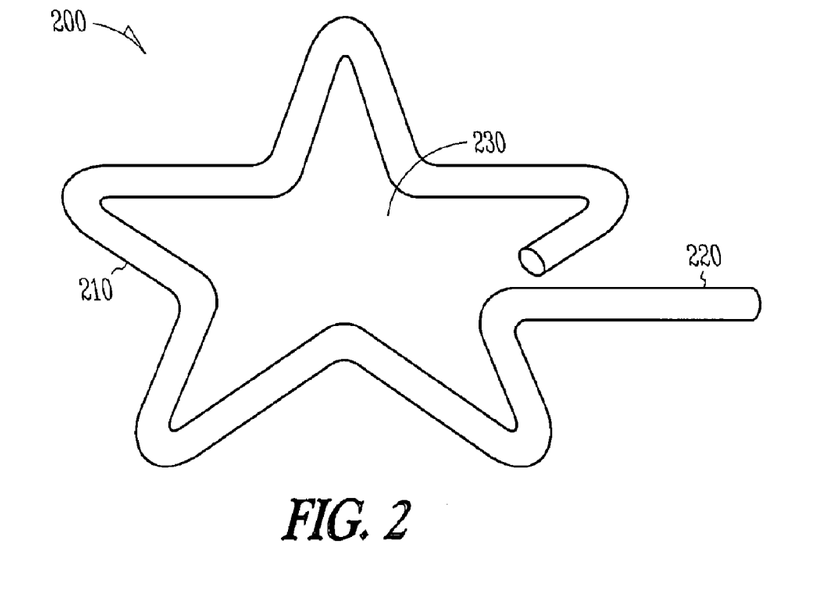
FIG. 2 is a sensor tip formed by wire bending in two dimensions according to an example embodiment.

FIG. 2 is a sensor tip 200 formed by wire bending in two dimensions according to an example embodiment. The electrode 220 is bent into a star shape, such that a mass is primarily located at the end 210 of electrode 220. Thereby obtaining the advantage, greater area of the ball 110 of FIG. 1, without the complicated step of welding the ball 110 onto the electrode 120. To increase the surface area of star 230 the star 230 is flattened means of forging, crimping, or other mechanical operation.

Figure 3:
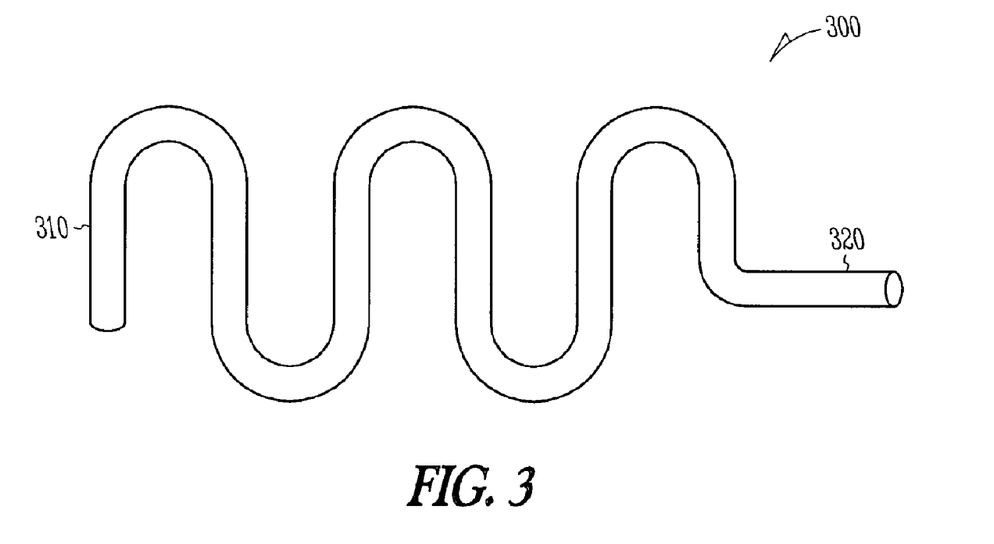
FIG. 3 is a sensor tip formed by wire bending in two dimensions according to an example embodiment.

FIG. 3 is a sensor tip 300 formed by wire bending in two dimensions according to an example embodiment. The electrode 320 of FIG. 3 is bent into a series of bends much in the form of a series of S's. Thereby as in FIG. 2 the end 310 of electrode 320 having a greater surface area.

Figure 4:
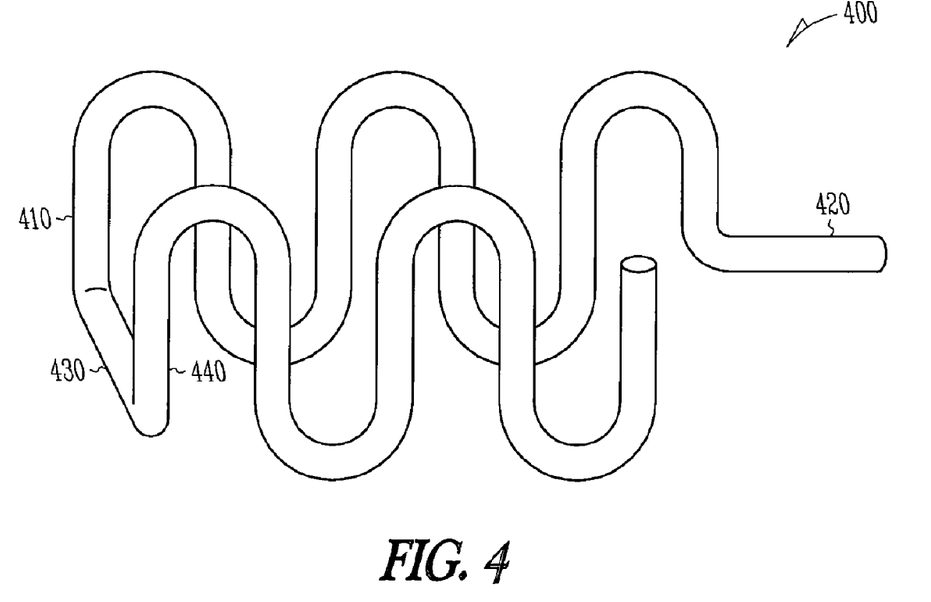
FIG. 4 is a sensor tip formed by wire bending in three dimensions according to an example embodiment.

FIG. 4 is a sensor tip 400 formed by wire bending in three dimensions according to an example embodiment. The electrode 420 of FIG. 4 is bent into a series of bends as with FIG. 3 in the form of a series of S's. At the end 410, a bend of ninety degrees provides a bridge 430 to a second series of S's 440. This shape provides for a greater volume increasing the effect noted with the ball on a stick.

Figure 5:
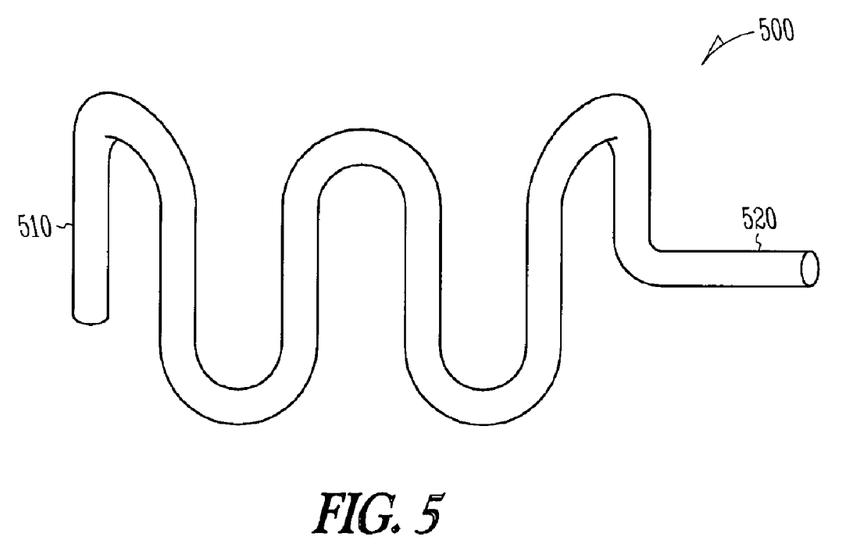
FIG. 5 is a sensor tip formed by wire bending in three dimensions according to an example embodiment.

FIG. 5 is a sensor tip 500 formed by wire bending in three dimensions according to an example embodiment. The electrode 520 is bent in a series of S's in one axis and then bent to form a circle to increase the volume at the end 510 of electrode 520.

Figure 6:
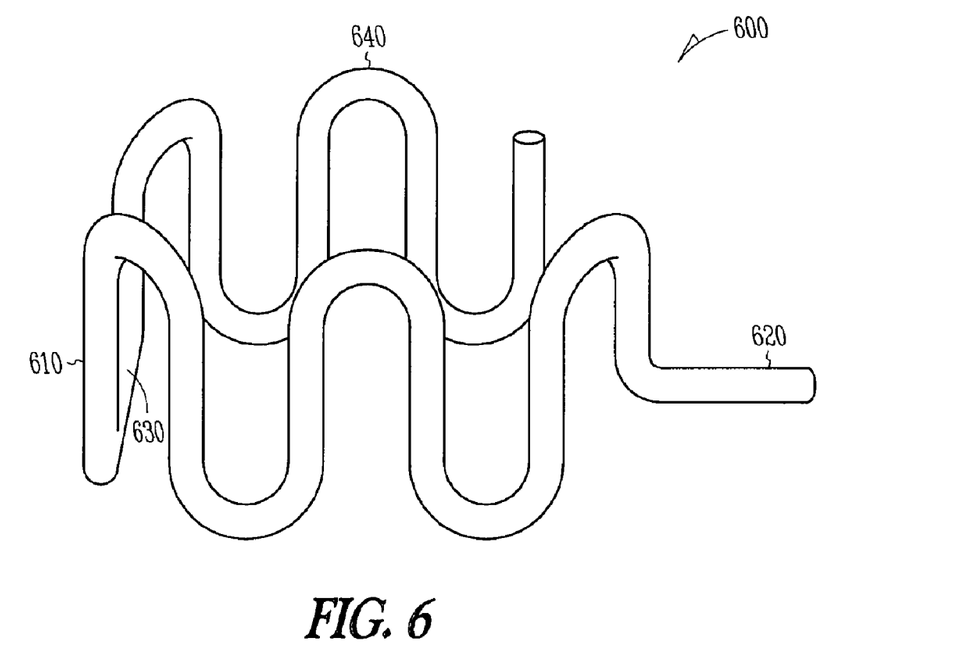
FIG. 6 is a sensor tip formed by wire bending in three dimensions according to an example embodiment.

FIG. 6 is a sensor tip 600 formed by wire bending in three dimensions according to an example embodiment. The electrode 620 is bent in a series of S's in one axis and then bent to form a circle to increase the volume at the end 610 of electrode 620. At the end 610 a bend of ninety degrees provides a bridge 630 to a second series of S's 640 that are also formed into a circle.

Figure 7:
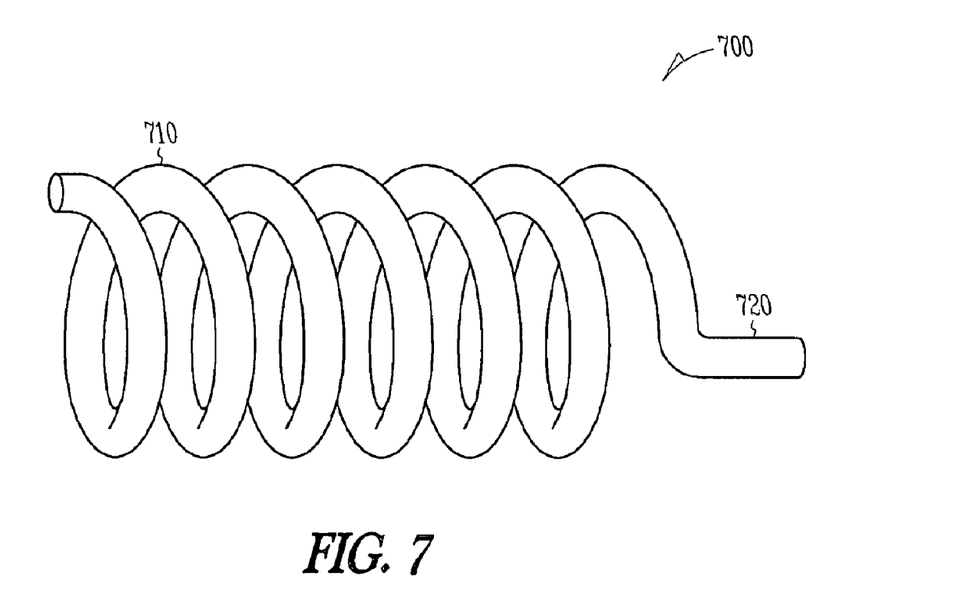
FIG. 7 is a sensor tip formed by wire bending the sensor end into a helical shape according to an example embodiment.

FIG. 7 is a sensor tip 700 formed by wire bending the sensor end into a helical shape according to an example embodiment. The electrode 720 is bent into a helical shape at the end 710. In addition each of the sensor tips illustrated in FIG. 2 through 6 may have increase surface area by flattening the rod 220, 320, 420, 520, 620, and 720 of FIGS. 2-7 respectively, by means of forging, crimping, or other mechanical operation. The various sensor tips are thus formed in multiple dimension shapes to increase the surface area of the tip at the end of the electrode.

Figure 8:
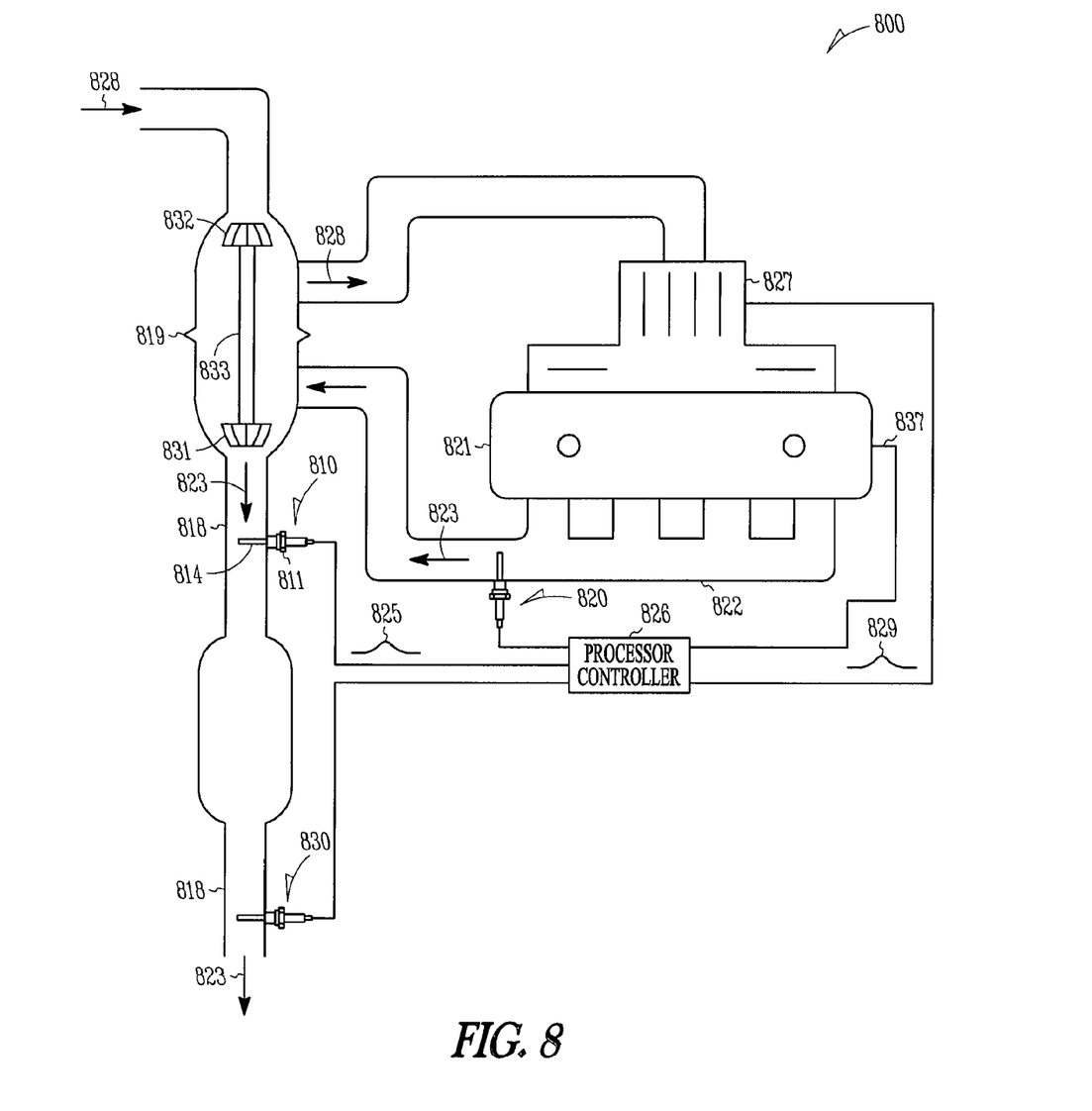
FIG. 8 is a system incorporating sensors of an example embodiment.

FIG. 8 is a system 800 incorporating sensors 810, 820 and 830 of an example embodiment. Sensor 810 may be installed in an exhaust pipe 818. There may be a stainless steel collar (not shown) welded into the exhaust pipe 818. The collar may be fabricated with an oversized threaded access so that the sensor 810 could be easily changed with other sensors 810 having different probe styles. Additional sensors 820 may be mounted in the exhaust manifold 822 upstream from turbocharger 819. Other sensors 830 may be mounted further down stream, for example about 2 meters, in exhaust pipe 818 from the turbocharger 819.

The additional sensors 820 and 830 may allow one to examine the effects of the turbocharger 819, such as strong mixing, and residence time on a signal from sensor 810. In the long term sites downstream from turbocharger 819 may be good locations because of the reduced risk of damage to the turbocharger 819 in the event of a sensor 810 failure. Signals 825, indicating an amount of particulate matter in the exhaust 823, on the line from sensor 810 may go to a processor and/or controller 826. Processor 826 may be connected to other particulate sensors 820 and 830, engine sensors, and a fuel injection and intake manifold system 827. Based on signals 825 from sensor 810 and possibly from sensors 820 and 830, sensors in system 827 and engine 821, for sensing some or all of, but not limited to, the following engine parameters (via line 837 to processor 826) such as fuel flow, EGR (exhaust gas recirculation), injection timing, needle lift, crankshaft angle, cylinder pressure, valve position and lift, manifold vacuum, fuel/air mixture, the intake properties of air 828 and other information from or about engine 821, processor 826 may provide control information signals 829 to the fuel injection amount and timing, EGR percent, valve control, and intake manifold system 827 and the like as desired, so as to cause engine 821 to expel a reduced amount of particulate emissions by adjusting fuel mixture, injection timing, percent EGR, valve control, and so forth. Incidentally, exhaust 823 may enter turbocharger 819 and cause a turbine 831 to spin and turn a compressor 832 via a shaft 833. Compressor 832 may compress incoming air 828 which goes in a more dense condition to system 827.

Initial concerns relative to sensor 810 were possible fouling by excessive soot and very high temperatures. However, operation of sensor 810 in an exhaust system has been reliable in view of operation of engine 821 under very heavy loads causing the observed exhaust 823 temperature to reach at least 670 degrees C. (1238 degrees F.) and resulting in a Bosch smoke number of exhaust 823 to be at least 5. The latter number may correspond to a particle mass concentration of 350 mg/m3.

Sensor 810 may put out a reproducible rms signal representing its image charge monitoring of the exhaust 823, which is correlated to exhaust smoke as characterized by the Bosch smoke number. Sensor 810 generally does not degrade due to soot build-up over a long period of time. Also, sensor 810 does not appear to degrade at various temperatures.

Figure 9:
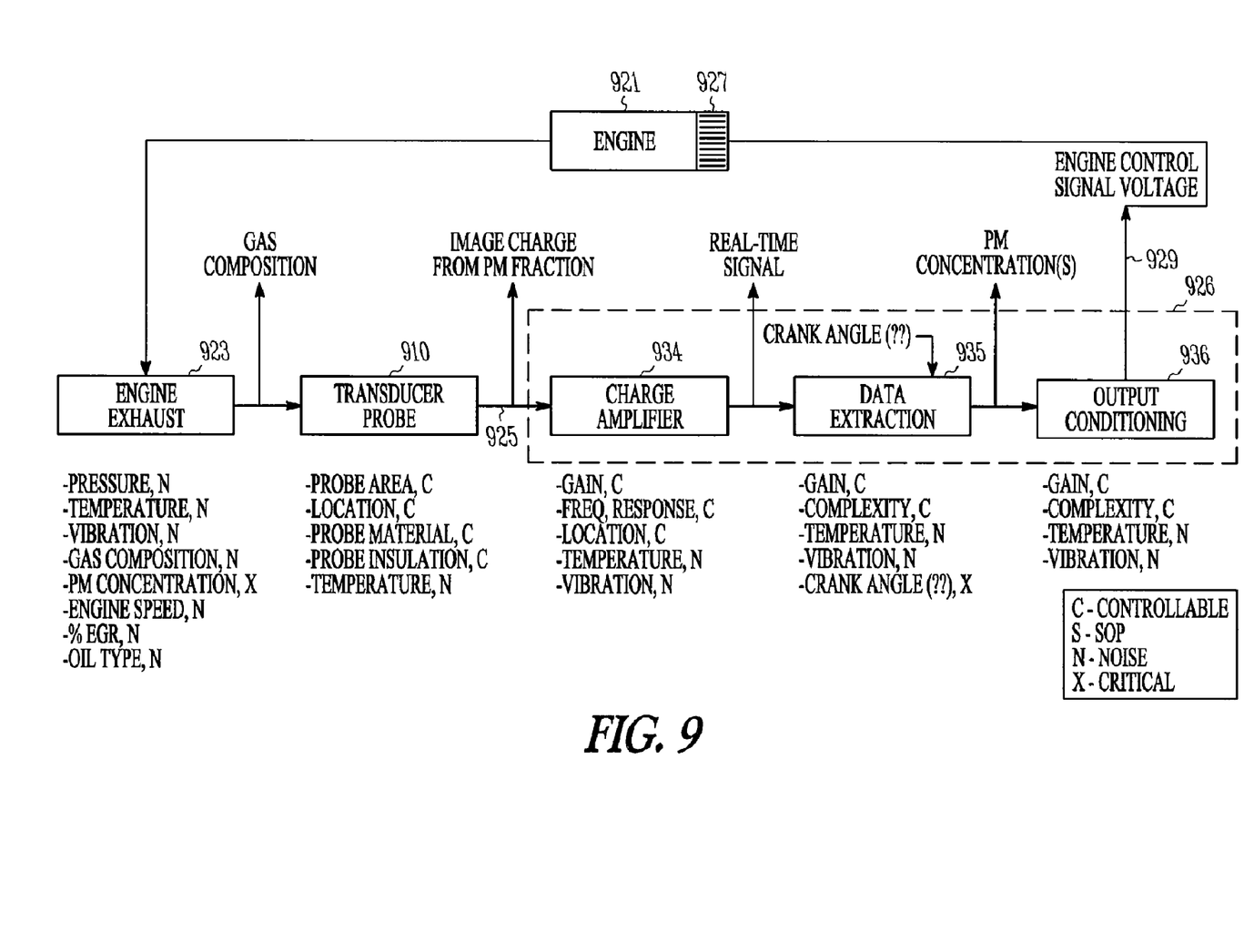
FIG. 9 a system incorporating a sensor of an example embodiment.

FIG. 9 a system incorporating a sensor of an example embodiment. FIG. 9 is one version of a loop for engine control based on the particulate matter of the exhaust emissions. Engine 921 may output an exhaust 923 which is sensed by sensor 910 which in turn may output an image charge signal 925 to processor 926 which may include an amplifier 934, a data extractor 935, and an output signal conditioner 936, among other components of the processor. Signal 925 may go to a charge amplifier 934 which may output a real-time signal to a data extraction device 935 which may receive a crankshaft angle determination. Components 934, 935 and 936 may have other parameter inputs for improving engine control and performance. The output from device 935 may include an electronic indication of the particulate matter concentration or concentrations. This signal may go to signal conditioning 936 which may, based on other various inputs of engine data (e.g. timing, temperature, percent EGR, valve position, and other engine information) provide engine control voltage signals 929 (for engine timing, percent EGR, valve control, and the like) to the fuel injection and manifold system 927 of engine 921.

Figure 10:
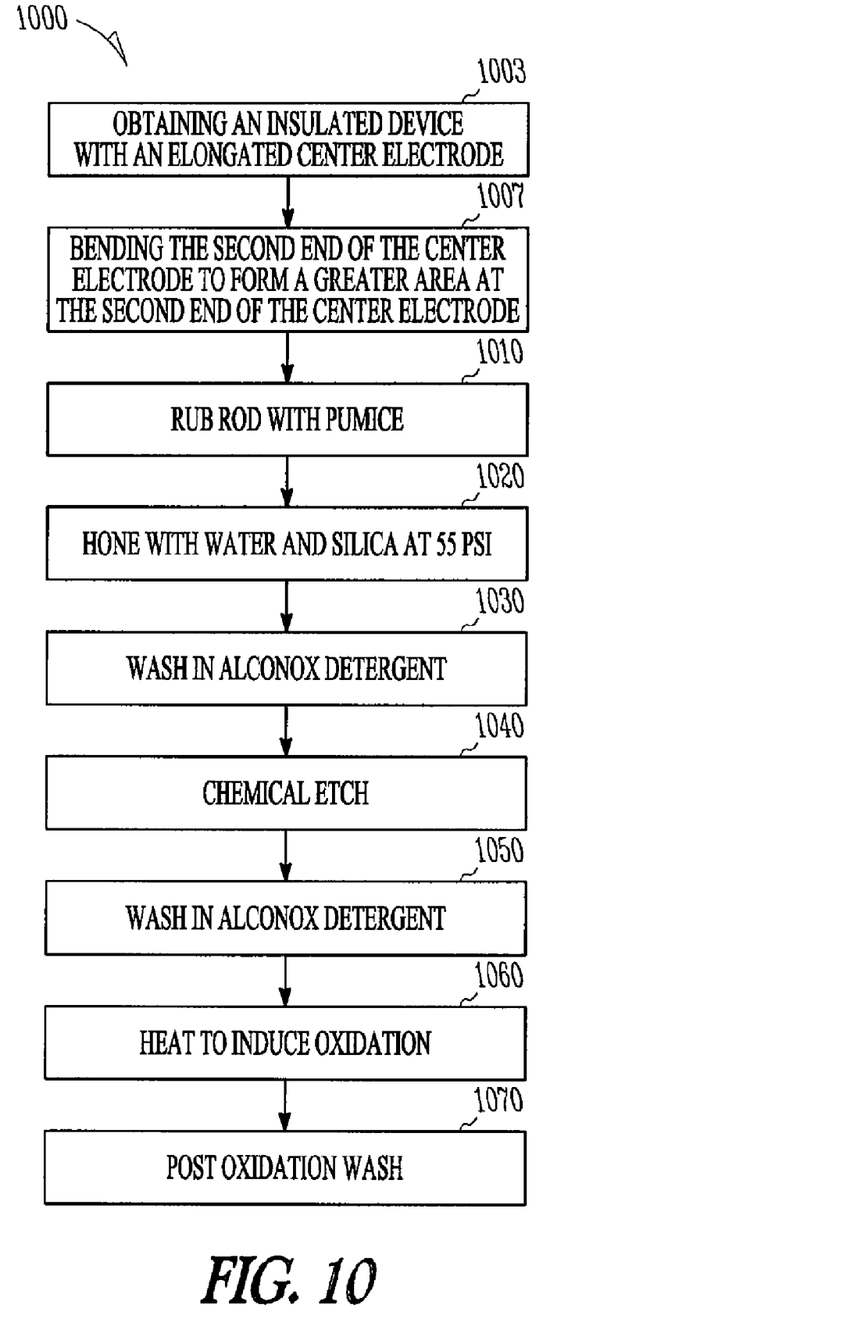
FIG. 10 is a method for making the sensor tips according to an example embodiment.

FIG. 10 is a method for making the sensor tips according to an example embodiment. The method 1000 takes an insulated device and forms an elongated electrode and then prepares the electrode to provide for a uniform oxidation layer and to formulate the oxidation layer. At 1003, an insulated device is obtained with an elongated electrode. The insulated device may be of a shape similar to a spark plug for a car with the center electrode either elongated from the terminal or soldered onto the center rod of the plug. As an alternative, rather than form the electrode while it is attached to the insulated device, the electrode may be formed following the steps, 1007 through 1070. Activity 1007 may be to bend the second end of the center electrode to form a enlarged surface area where the electrode will come in contact with the exhaust.

At 1010 once the rod or sensor has been bent into the desired configuration and the rod has been flattened, the rod is rubbed with a pumice. The electrodes are mechanically scrubbed and honed to remove any oxide scale that exists on the rods. This will increase the uniformity of the subsequent etching process.

Activity 1020 may be to hone the electrode with a wet blast using a mixture of water and silica abrasive at 55 pounds per square inch of pressure. A silica size of 7/0 was found to be suitable. This step cleans the electrodes prior to etching. Activity 1030 may be to then wash the electrodes in alconox, or other suitable detergent, to prevent contamination of the etch solution. Activity 1040 may be to chemically etch the electrodes in a ferric chloride solution to remove inclusions and micro-roughen the surface for improved oxide adhesion. Activity 1050 is to rinse the electrodes and then wash the electrodes in an alconox detergent with ultrasonic vibrations to remove any impurities or debris left on the surface. The electrodes are then thoroughly rinsed to remove any chemical contamination. The electrodes are then dipped in acetone and blown dry with filtered nitrogen to minimize staining.

Activity 1060 may be to place the electrodes on quartz boats and heat the electrodes to induce oxidation. The electrodes are oxidized at elevated temperatures in air to form aluminum oxide (alumina/$Al_2O_3$) scale. The aluminum within the alloy supplies the metal for the alumina formation. The alumina provides oxidation protection and electrical insulation. One embodiment is to use an oxidation temperature of 1200° C. and for 14 hours. The alumina oxide will form at lower temperatures and shorter times, but higher temperatures form a more dense coating and longer times form thicker coatings which have superior insulation properties. The inventors have noted that these alloys typically have melting points between 1350° C. and 1450° C. and temperatures above 1200° C. typically result in the metal sagging and shape deformation.

Activity 1070 may be for the electrodes to be rinsed in flowing deionized water for 10 minutes and blown dry with nitrogen.

The inventors have shown that super alloys have a native oxide with insulating properties suitable for construction of particulate matter sensor electrodes. Super alloys contain aluminum as an alloying addition. When heated in air at high temperatures, the aluminum forms a surface dielectric layer. Since the aluminum has a high diffusivity in the alloys, this surface oxide can be thick. For example, fecralloy, oxidized at 1200° C. for fourteen hours, was found to have a breakdown voltage of 280.3±67.5 volts and an insulation resistance of 41.6±14.9 mega ohms when measured at 850° C.

Common iron-based super alloys include fecralloy (Resistalloy International), Kanthal-AF (Kanthal/Sandvik Corp.), Kanthal-A1 (Kanthal/Sandvik Corp.), Aluchrome-O (Thyssen-Krupp VDM), Alkrothal-14 ((Kanthal/Sandvik Corp.), and Haynes 214 (Haynes International). A representative nickel-based super alloy is Mar-M-247 (Martin Marietta Materials). The inventors have determined that super alloys oxidized at 1200° C. for fourteen hours were found to have electrical insulating properties at 500° C. These properties included dielectric breakdown strength greater than 25 volts, and insulation resistance greater than 1 megohm. Microscopy of cross-sections of oxidized alloys gave the following oxide thickness values for oxidation under this condition. Table 1 illustrates the thickness of the oxides for various alloy types.

TABLE 1

| Alloy Type | Oxide Thickness (micrometer) |
| --- | --- |
| FeCrAlloy | 6.35 ± 2.22 |
| Kanthal-AF | 4.80 ± 1.43 |
| Kanthal-A1 | 5.45 ± 2.18 |
| Aluchrome-O | 4.56 ± 1.64 |
| Alkrothal-720 | 9.26 ± 3.21 |
| Haynes 214 | 3.51 ± 1.01 |

Oxide thickness in this range is sufficient for particulate matter sensor electrodes operating at high temperatures, although oxide thickness of about one micrometer may be suitable for some applications, especially those at lower temperature. Greater oxide thickness in the range of 5-20 micrometers may also be suitable, but oxide thickness greater than about twenty micrometers should be avoided, since the thermal stress at the oxide-alloy interface may promote spallation of the insulating oxide. The maximum oxide thickness for reduction or elimination of oxide spallation will depend on the particular alloy selected, the intended application, and geometry of the electrode.

The Abstract of the Disclosure is provided to comply with 37 C.F.R. §1.72(b) requiring an abstract that will allow the reader to quickly ascertain the nature of the technical disclosure. It is submitted with the understanding that it will not be used to interpret or limit the scope or meaning of the claims. The above description and figures illustrate embodiments of the invention to enable those skilled in the art to practice the embodiments of the invention. Thus the following claims are hereby incorporated into the Detailed Description, with each claim standing on its own as a separate embodiment.

What is claimed is:

1. A particulate matter detector comprising:
    an insulated device; and
    a center electrode having a first end and a second end wherein the first end of the center electrode passes through the insulated device and the second end of the electrode is bent, without welding, to provide an increased surface area and to detect the particulate matter.

2. The detector of claim 1, wherein the second end of the electrode is formed into a star shape.

3. The detector of claim 1, wherein the second end of the electrode is formed into a series of bends in an s shape.

4. The detector of claim 1, wherein the second end of the electrode is formed into a series of bends in an s shape having a bend to a second series of bends in an s shape.

5. The detector of claim 1, wherein the second end of the electrode is formed into a helix.

6. The detector of claim 1, wherein the second end of the electrode is flattened.

7. The detector of claim 1 wherein:
    the center electrode has a length between 0.25 inch and 12 inches; and
    the center electrode has a thickness between 1/32 inch and 3/8 inch.

8. The detector of claim 1, wherein:
the insulated device has a terminal connected to the first end of the center electrode; and
the terminal is connected to an amplifier having an output that may indicate a particulate concentration in a vicinity of the second end of the electrode.

9. The detector of claim 8, wherein the second end of the center electrode is situated in a portion of a combustion mechanism.

10. The detector of claim 1 wherein the electrode is formed of one of an iron-chrome alloy, a Kanthal-AF, a Kanthal-AL, an Aluchrome-O, an Alkrothal-720, Haynes 214 or an aluminum containing alloy.

11. The detector of claim 1, wherein the electrode is bent into a three dimensional shape.

* * * * *